(12) United States Patent
Sudarsky et al.

(10) Patent No.: US 10,593,099 B2
(45) Date of Patent: Mar. 17, 2020

(54) TRANSFER FUNCTION DETERMINATION IN MEDICAL IMAGING (71) Applicant: Siemens Healthcare GmbH, Erlangen (DE)

(72) Inventors: Sandra Sudarsky, Bedminster, NJ (US); Kaloian Petkov, Lawrenceville, NJ (US)

(73) Assignee: Siemens Healthcare GmbH, Erlangen (DE)

(*) Notice: Subject to any disclaimer, the term of this patent is extended or adjusted under 35 U.S.C. 154(b) by 23 days.

(21) Appl. No.: 15/811,796

(22) Filed: Nov. 14, 2017

(65) Prior Publication Data
US 2019/0147639 A1 May 16, 2019

(51) Int. Cl.
G06T 15/08 (2011.01)
A61B 5/107 (2006.01)
A61B 5/00 (2006.01)
G06T 11/00 (2006.01)
G06T 7/00 (2017.01)
A61B 5/055 (2006.01)

(52) U.S. Cl.
CPC ............ G06T 15/08 (2013.01); A61B 5/0033 (2013.01); A61B 5/055 (2013.01); A61B 5/1073 (2013.01); G06T 7/0012 (2013.01); G06T 11/008 (2013.01); G06T 2207/10081 (2013.01); G06T 2207/10088 (2013.01); G06T 2207/10108 (2013.01); G06T 2207/10132 (2013.01); G06T 2207/20104 (2013.01); G06T 2210/41 (2013.01)

(58) Field of Classification Search
CPC ..... G06T 15/08; G06T 7/0012; G06T 11/008; G06T 2207/10081; G06T 2207/10088; G06T 2207/10108; G06T 2207/10132; G06T 2207/20104; A61B 5/1073
USPC ........................................................ 345/424
See application file for complete search history.

(56) References Cited

U.S. PATENT DOCUMENTS

| 9,760,690 | B1 | 9/2017 | Petkov et al. | |
| 2001/0055016 | A1* | 12/2001 | Krishnan | G06T 15/08 345/424 |
| 2005/0074155 | A1 | 4/2005 | Alyassin | |
| 2007/0274583 | A1* | 11/2007 | Sugiyama | G06T 11/008 382/131 |
| 2009/0002369 | A1* | 1/2009 | Rottger | G06T 15/08 345/424 |

(Continued)

OTHER PUBLICATIONS

Engel, K., 2016. Real-Time Monte-Carlo Path Tracing of Medical Volume Data, GPU Technology Conference, Apr. 4-7, 2016, San Jose Convention Center, CA, USA.

(Continued)

Primary Examiner — King Y Poon
Assistant Examiner — Vincent Peren (57) ABSTRACT

For rendering in medical imaging, a transfer function is determined. A simple approach to setting the transfer function uses a combination of a rendered image and the voxel data, providing a hybrid of both image and data-driven approaches. A region of interest on a rendered image is used to select some of the voxel data. A characteristic of the selected voxel data is used to determine the transfer function for rendering another image. Both the visual aspect of the rendered image and the voxel data from the scan are used to set the transfer function.

19 Claims, 9 Drawing Sheets
(7 of 9 Drawing Sheet(s) Filed in Color)

(56) References Cited

U.S. PATENT DOCUMENTS

2010/0014729 A1    1/2010  Choi et al.
2016/0269723 A1*   9/2016  Zhou ...................... G06T 15/06

OTHER PUBLICATIONS

He, Taosong, et al. "Generation of transfer functions with stochastic search techniques." Visualization'96. Proceedings.. IEEE, 1996.
Kindlmann, Gordon, and James W. Durkin. "Semi-automatic generation of transfer functions for direct volume rendering." Proceedings of the 1998 IEEE symposium on Volume visualization. ACM, 1998.
Kniss, Joe, Gordon Kindlmann, and Charles Hansen. "Multidimensional transfer functions for interactive volume rendering." IEEE Transactions on visualization and computer graphics 8.3 (2002): 270-285.
Ljung, Patric, et al. "State of the art in transfer functions for direct volume rendering." Computer Graphics Forum. vol. 35. No. 3. 2016.
Marks, Joe, et al. "Design galleries: A general approach to setting parameters for computer graphics and animation." Proceedings of the 24th annual conference on Computer graphics and interactive techniques. ACM Press/Addison-Wesley Publishing Co., 1997.
Rezk-Salama, C., Hastreiter, P., Scherer, J., & Greiner, G. (2000). Automatic Adjustment of Transfer Functions for 3D Volume Visualization. In VMV (pp. 357-364).
Partial European Search Report dated Apr. 16, 2019 in corresponding European patent application No. 18205592.1.
Gunnar Lathen et al: "Automatie Tuning of Spatially Varying Transfer Functions for Blood Vessel Visualization", EEE Transactions On Visualization And Computer Graphics, IEEE Service Center, Los Alamitos, CA, US, vol. 18, No. 12, Dec. 1, 2012 (Dec. 1, 2012), pp. 2345-2354.
Johnson PT et al: " CT angiography with volume rendering: advantages and applications in splanchnic vascular imaging", Radiology, Radiological Society of North America, Inc, US, vol. 200. No. 2, Aug. 1, 1996 (Aug. 1, 1996), pp. 564-568.

* cited by examiner

TRANSFER FUNCTION DETERMINATION IN MEDICAL IMAGING

BACKGROUND

The present embodiments relate to volume rendering in medical imaging. For volume rendering, the transfer function specifies a mapping between the volumetric scalar data and the optical properties of the rendered image, such as color and opacity. In medical applications, task dependent transfer functions, also known as presets, are used to optimize the display of specific anatomical regions or to emphasize specific tissue types. Most volume rendering systems offer the functionality to manually adjust the parameters of the transfer function. The window width may specify the range of scalar values mapped and determines the contrast of the rendered image, and the window level centers the transfer function around a particular value of interest. Different combinations of the window width and level parameters lead to different findings and have to be adjusted repeatedly to improve the diagnostic information present in the image. Due to the complex and often unpredictable relationship between a transfer function and the resulting image, this manual adjustment is difficult and time consuming.

Automated techniques may simplify adjustment or setting of the transfer function. Image-driven approaches analyze the images generated with different parameters to select the optimal settings. For example, the user selects the best set of images, and a stochastic search is invoked to generate a new set of transfer functions based on the selection. Data-driven approaches analyze the volumetric data instead of the generated images. Although these approaches are widely used at research facilities, they are not commonly accepted in clinical practice as they are not intuitive or easy to use.

SUMMARY

By way of introduction, the preferred embodiments described below include methods, systems, instructions, and computer readable media for rendering in medical imaging, such as by determining a transfer function for rendering. A simple approach to setting the transfer function uses a combination of a rendered image and the voxel data, providing a hybrid of both the image and data-driven approaches. A region of interest on a rendered image is used to select some of the voxel data. A characteristic of the selected voxel data is used to determine the transfer function for rendering another image. Both the visual aspect of the rendered image and the voxel data from the scan are used to set the transfer function.

In a first aspect, a method is provided for determining a transfer function for rendering an image from a medical scanner. A medical scanner scans a volume of a patient. The scanning provides intensities representing voxels of the volume. A graphics processing unit renders, using a first transfer function, a first two-dimensional image from the intensities representing the voxels. A region of interest determined based on the first two-dimensional image is received, and a subset of the voxels are identified based on the region of interest. A second transfer function (e.g., new transfer function in the sense of having a different value for one or more parameters) is determined from a distribution of the intensities of the voxels of the subset. The graphics processing unit renders a second two-dimensional image using the second transfer function.

In a second aspect, a system is provided for rendering in medical imaging. A medical imaging system is configured to scan an internal region of a patient and generate voxel data representing a volume comprising the internal region. A renderer is configured to render a first image from the voxel data. The renderer is configured to render with a transfer function setting based on part of the voxel data selected with a region in a second image. A display is configured to display the image output by the renderer. The image represents the internal region.

In a third aspect, a method is provided for rendering in medical imaging. A medical scanner scans a volume of a patient, providing intensities representing voxels of the volume. A graphics processing unit renders, using a first transfer function, a first two-dimensional image from the intensities representing the voxels. The graphics processing unit renders a second two-dimensional image using a second transfer function. The second transfer function is set as a function of the intensities of a subset of the voxels corresponding to a region of interest on the first two-dimensional image and a depth of a surface depicted in the first two-dimensional image.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Automated transfer function design allows for interactive volume exploration in a clinical setting. A simple and intuitive method is based on the selection of one or more regions of interest (ROIs) to design the transfer functions, simplifying the exploration of volumetric data sets. The optimal set of windowing parameters to render images is automatically computed.

A hybrid technique based on ROIs specified on a rendered image together with a histogram analysis of the corresponding scalar voxel values is used to define or adjust the transfer function. Given a scalar volume and a transfer function, the user or system sets the rendering elements, including lights, cut planes and the virtual camera to generate a rendered image. A region of interest, specified either manually or automatically, triggers the generation of a depth map or an update to a voxel cache and the calculation of the local histogram. The same way that a depth map stores, for every pixel, the distance to the object to the virtual camera, the scalar values of the corresponding voxel in the volume are cached, allowing efficient construction of the histogram for the given ROI.

The histogram is used to determine the transfer function. The ROI provides an indication of a region that is lacking, such as not having sufficient contrast. The tissue may have a similar intensity as other tissue, so is rendered in a similar color. To provide more contrast, the transfer function is set based on the voxels for that tissue designated by the ROI. The transfer function may be set to increase the contrast within the selected region. In another embodiment, the transparency mapped from the transfer function is increased, revealing anatomical structures occluded by the tissue of the ROI. The placement of the ROI facilitates exploration of the volumetric data set by interactively defining new transfer functions.

Figure 1:
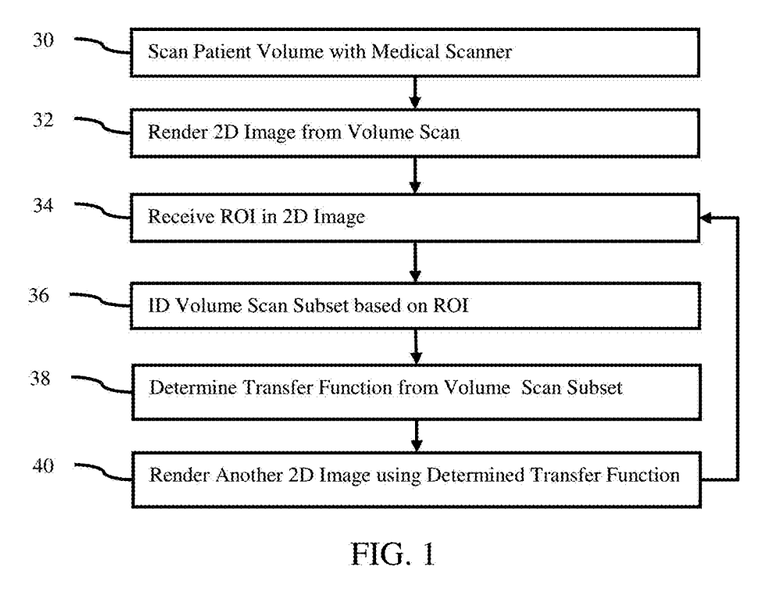
FIG. 1 is a flow chart diagram of one embodiment of a method for rendering in medical imaging.

FIG. 1 shows one embodiment of a method for rendering in medical imaging. A ROI on a rendered image is used to indicate imaged structure that occludes, has insufficient contrast, or is of interest. Scan data representing a volume is selected based on the ROI and used to reset the transfer function. By rendering with the reset transfer function, the resulting image may have more contrast, less occlusion, and/or improved visualization of the structure of interest.

Figure 2:
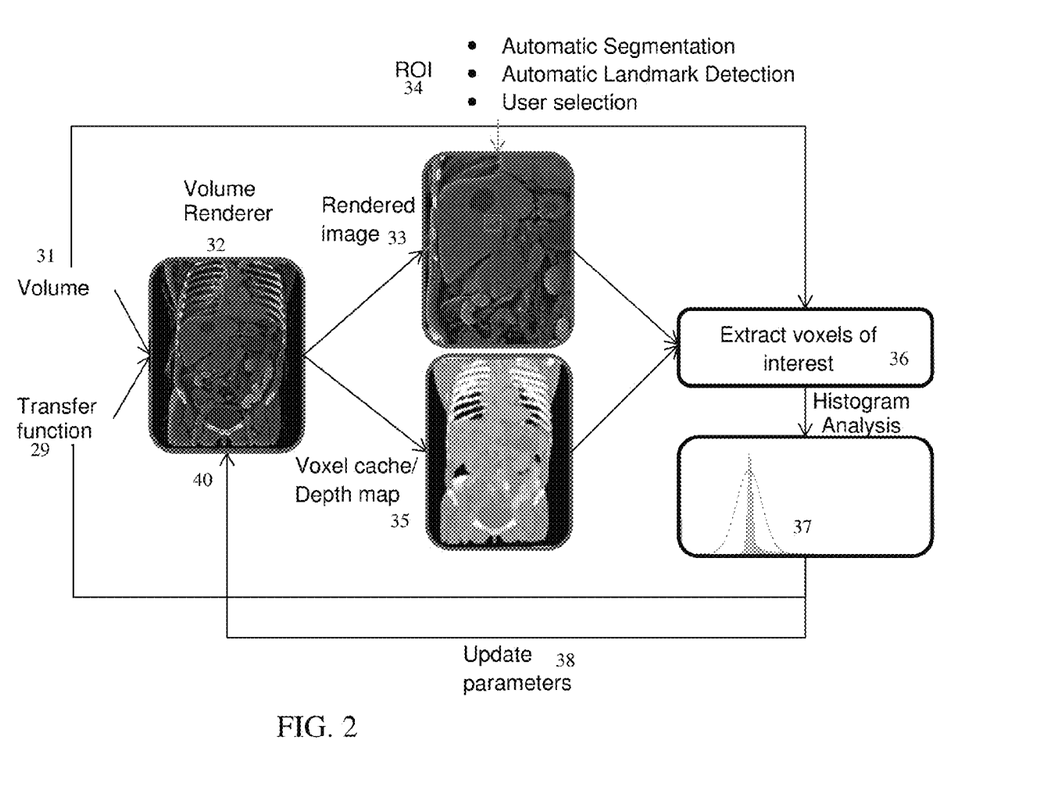
FIG. 2 is a flow chart diagram of one embodiment of a method for determining a transfer function for rendering an image.

FIG. 2 shows another embodiment of the method for rendering in medical imaging. The transfer function is determined using a hybrid of information from a rendered image and information from unrendered scan data. FIGS. 1 and 2 are described together.

Figure 15:
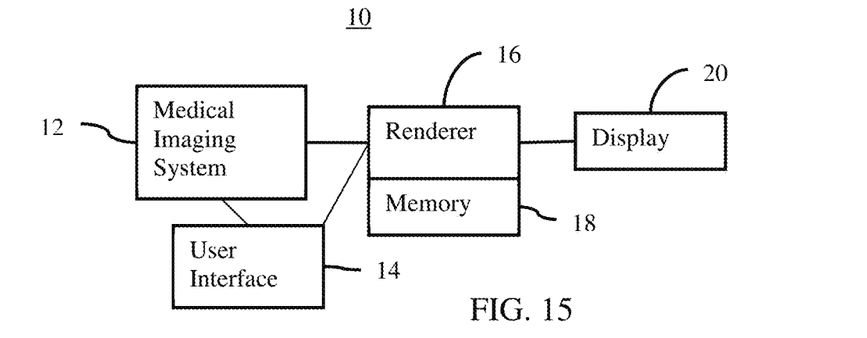
FIG. 15 is a block diagram of one embodiment of a system for rendering in medical imaging.

The methods are implemented by the system 10 of FIG. 15 or another system. For example, act 30 is performed by a medical scanner, and acts 32-40 are performed by a renderer, server, image processor, or another processor. Any one or more of the acts may be performed by different devices. A user interface or input device may be used for act 34.

The acts are performed in the order shown or other orders. Additional, different, or fewer acts may be provided. For example, the repetition from act 40 to act 34 in FIG. 1 is not provided. As another example, act 40 is a repetition of act 32, as shown in FIG. 2. In another example, act 30 is not performed. Instead, the scan data is loaded from a memory or received by transfer over a computer network.

An initial image is rendered with a transfer function set in any manner. This initial image may be a first image or is merely initial due to being a previous image. Another transfer function is determined based on a ROI in the initial image and used to render another image. The same scan data is used to render both images. Alternatively, the scanning is on-going or repeats. Different scan data is used to render the different images. The scan data from the initial image is used to determine the transfer function used to render from different or subsequently acquired scan data.

In act 30, a medical scanner acquires a set of voxels. The set represents a volume of the patient. The volume of a patient is scanned with the medical scanner. The interior of the patient is scanned, such as with magnetic resonance (MR), x-ray (e.g., computed tomography (CT)), ultrasound, or emission tomography (e.g., positron emission tomography (PET) or single photon emission computed tomography (SPECT)). The scan is performed in any format, such as detecting emissions along lines of response, acquiring k-space data at magnetic gradient defined locations, or acquiring projections through the patient with x-rays from different directions.

A renderer or the medical imaging system reconstructs a volume 31 representing, at least in part, the internal portion of the patient. Any reconstruction from the scan data may be used. Tomography or other process may be used to determine intensities for different locations (i.e., voxels) distributed in three dimensions. As a result of the scan, data representing the interior of the patient in an N×M×O region or volume is acquired, where N, M, and O are integers greater than 1. The reconstruction determines scalar values or intensities for each of a plurality of voxels distributed in three dimensions.

The intensities represent response from blood, tissue, bone, other object, and/or contrast agents in the patient. Anatomy and/or an inserted object are represented. In another embodiment, scan data representing a torso or specific organ is acquired. Other information may be included, such as response from fluid or other structures.

The scan or voxel data is acquired by scanning. The output from the medical scanner may be rendered in real-time with the scanning or during an appointment of a patient. Alternatively, the scan or voxel data is stored, such as in a picture archiving communications system (PACS) or patient medical record database. The stored scan data is loaded from memory for rendering.

In act 32, a graphics processing unit renders a two-dimensional image 33 from the intensities representing the voxels. The three-dimensional distribution of voxels or intensities is rendered to a two-dimensional image 33 for display. The pixel values of the two-dimensional image 33 are determined from the voxel values of the three-dimensional distribution. The pixels values may then be used on the two-dimensional screen or display.

Multi-modal datasets may be rendered. Scan data from scans of different modalities of scanning (i.e., different types of medical scanners) may be rendered together or rendered separately and combined.

Any now known or later type of volume rendering may be used. For example, volume ray casting is used. Ray casting projects rays through a volume, such as casting a ray from each pixel of an image plane in parallel or from a view point through the volume. The intensities along each ray are examined to create a pixel value for the image. For example, in maximum intensity projection, the maximum intensity along each ray is found and used. As another example, the intensities along the ray are combined in a weighted average, where the weight is based on opacity or magnitude of the intensity. Alpha blending may be used.

In another embodiment, ray tracing is used. Ray tracing is used in physically-based or cinematic rendering to generate photo-realistic images. Rays are projected from each pixel. Light photons are simulated along each of the rays. The scattering, absorption, and/or emission of the light photons may be simulated. The path of the ray may divert due to scattering, providing tracing of the ray through the volume along different paths rather than just the rays from each pixel. Many photons are simulated for each ray. The color or intensity resulting from the scattering, absorption, and/or emission along each ray is calculated. To physically render the image, probabilities are solved. The probabilities model the interaction of the photons with intensities for the different locations in the volume. For example, Monte Carlo emulation of the photon interaction is used in the rendering. In Monte Carlo-based physical rendering, contribution from the volume samples to the final image are based on simulation of interactions between light photons projected from the viewpoint to the volume structure along the ray paths. The probabilities are solved for along each of a plurality of rays traced from pixels with Monte Carlo ray tracing.

The rendering uses a transfer function 29. The transfer function 29 is a color map used to assign color to scalar values of the scan data. One or more characteristics distinguish one transfer function 29 from another. The characteristics include the color map or pallet, the opacity (or transparency) level, transparency range or variation, a window width, and/or a window level. The color map controls what colors are assigned to the scalar values. FIGS. 3-6 shows a black, red, and white color pallet. The opacity controls the level of transparency or contribution of any color. The opacity may be one value or may be a range of scalar values over which a given opacity is used. The window width controls the dynamic range or size of the window where colors other than the extremes (e.g., black and white in the example of FIGS. 3-6) are used. The window level controls the center of the window along the range of scalar values (e.g., along the x-axis of the transfer functions of FIGS. 3-6). Other characteristics include the function for distribution of colors within the window. In the examples of FIGS. 3-6, a linear function is used, as represented by the line and the corresponding equal distribution of different colors through the window. In other embodiments, the function is non-linear so that one range of scalar values maps to fewer colors than the same size range at a different location within the window.

The rendering is onto a display device. The rendering assigns red, green, blue (RGB) or other values to pixels. The values are formatted for display and stored in a display buffer. The display is configured by reading the display buffer, generating the image on the display device. The rendered image 33 or images are displayed by the renderer on the display. The image 33 represents the patient with or without any inserted objects. Alternatively, the image is transmitted to a network or memory, such as a picture archiving communications system.

In act 34, the graphics processing unit, medical scanner, and/or processor receives a ROI designation. The receipt is from a user interface, such as a user input device. Alternatively, the receipt is from a processor, such as an image or control processor, or from a memory.

The ROI designation defines a spatial extent of the ROI. The ROI is a box, oval, circle, or other area designator. The ROI is determined based on the two-dimensional image 33. The ROI designates with respect to the image 33. The image 33 as displayed is used to determine the ROI.

Figure 7:
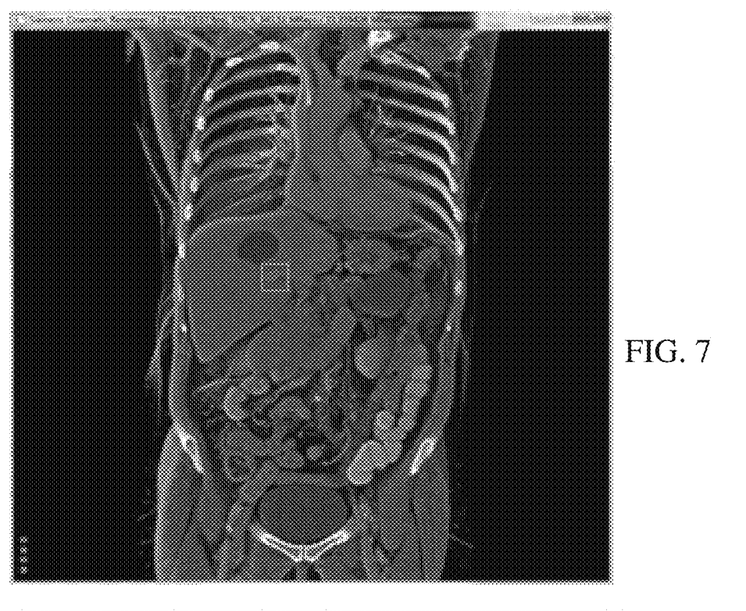
FIGS. 7 and 8 show example rendered images using the transfer functions of FIGS. 3 and 4, respectively.

In one embodiment, the ROI designation is received as a user selection with a user input device. The user views the image 33. Using the user input device (e.g., trackball or mouse), the user positions and/or sizes the ROI. FIG. 7 shows an example with a square ROI shown as a green box. The position is on tissue of interest, such as tissue with less contrast than desired. FIG. 7 shows the liver as having similar color as other organs. The ROI may be positioned based on occlusion, such as wanting to better view information behind the liver tissue at the ROI.

In another embodiment, the ROI designation is received as automated detection of the ROI and/or landmarks defining the ROI. Segmentation may be used to position the ROI, such as the ROI being a border of detected anatomy. Landmarks may be used to position the ROI, such as positioning the ROI at a set location and size relative to any number of detected landmarks. Any segmentation or landmark detection may be used. The automatic detection may use contrast, occlusion, or other information. The automatic detection is applied to the two-dimensional image 33 without being applied to the scan data. Alternatively, the detection is applied to both the two-dimensional image 33 and the scan data. The ROI may be predefined, such as at a default location.

In act 36, the graphics processing unit, medical scanner, and/or processor identifies a subset of the voxels based on the ROI. The ROI is an area on a two-dimensional image. That area may be extended in depth (i.e., towards and/or away from the viewer) to define a sub-volume of the volume 31. The voxels representing the sub-volume are identified as the subset of all the voxels of the volume 31.

In one embodiment, the subset is identified from a voxel cache or depth map 35. The depth map provides, for each pixel, a depth at which a given opacity occurs. Any depth test to define the depth may be used. For example, the opacity (e.g., a value) is used. As another example, a gradient test is performed to find a first gradient above a threshold in the intensities or scalar values traveling from a virtual viewer through the volume.

The ROI provides lateral positions corresponding to a group of pixels included in the ROI. The depth map 35 defines a depth for each lateral position. The depth and lateral position define a voxel. The intensity or scalar value from the scan data for the defined voxels are loaded from a voxel cache. Alternatively, the voxel cache includes the depth map, so the voxel cache is used to determine the intensities for the identified subset of voxels.

In act 38, the graphics processing unit, medical scanner, and/or processor determines another transfer function 29 to use for rendering in act 40 (or a repeat of act 32). The new transfer function has one or more characteristics changed, such as the window level, window width, color pallet, opacity, and/or opacity range. The new transfer function may be the same color transfer function, but with different settings for one or more parameters of the transfer function (e.g., different window width). Other characteristics are the same or unchanged.

The new transfer function 29 is determined from a characteristic of the intensities of the voxels of the subset. Any characteristic of the intensities may be used, such as a gradient, variance, or curvature (e.g., spatial distribution of structure in the intensities). In one embodiment, a distribution of the intensities of the voxels of the subset is used. The distribution is represented by a histogram 37 of scalar values. The number of occurrences of each scalar value or each range of scalar values forms a histogram 37.

The histogram 37 is used as the distribution. Alternatively, a curve is fit to the histogram 37 and used as the distribution. Any curve or type of curve may be fit. For example, a Gaussian curve is fit to the number of intensities for each scalar value in the histogram 37. In order to remove outliers that accidentally fall within the ROI, the characteristics of the fit Gaussian curve are used, ignoring values that lie (e.g., 1, 2, or 3) standard deviations away from the mean. The fit curve has various characteristics, such as a mean and standard deviation. μ is the mean, and σ is the standard deviation of the fitted curve. These characteristics may be used as the distribution.

The distribution is mapped to values for settings of the transfer function 29. The new transfer function 29 is created by setting a characteristic of the transfer function 29 differently than used for the initial rendering in act 32. More than one characteristic may be changed.

In one embodiment, the window width and/or window level are changed. The change is to increase contrast for the tissue or structure of the ROI. To increase contrast, the window is centered by a mean for the intensities of the voxels identified by the ROI, and/or the window width is reduced to map the full range of colors to a smaller range of scalar values.

Any function may be used to map the distribution to the window level and/or width. For example, the window width is determined from a mean and standard deviation of the Gaussian curve and a window width of the initial transfer function, and the window level is determined from the window width of the second transfer function, the mean, and the window width of the first transfer function. One possible function to map the window width, W'w, is:

$$W'w = (roiMax - roiMin)/(lutMax - lutMin)$$

One possible function to map the window level, W'l, is:

$$W'l = \mu - (lutMax + LutMin)/2 * W'w$$

where $roiMin = \mu - 2\sigma$ and $roiMax = \mu + 2\sigma$, and lutMax and lutMin are the maximum and minimum of the window from the initial transfer function 29. The difference in lutMax and lutMin is the window width of the initial transfer function.

Other functions or mappings from distribution to window level and/or width may be used. For example, the histogram may not follow a normal or Gaussian distribution, such as where two distributions of any shape are separated by a region of scalar values without occurrence (i.e., fully transparent). The characteristics of the distribution are mapped in a non-linear look-up table to the characteristics of the transfer function 29.

Figure 3:
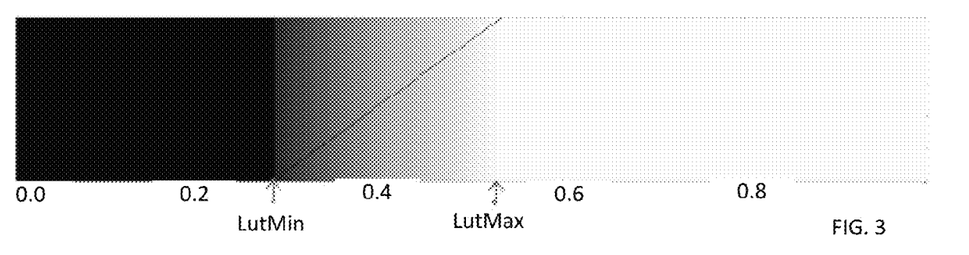
FIGS. 3 and 4 show example transfer functions.
Figure 5:
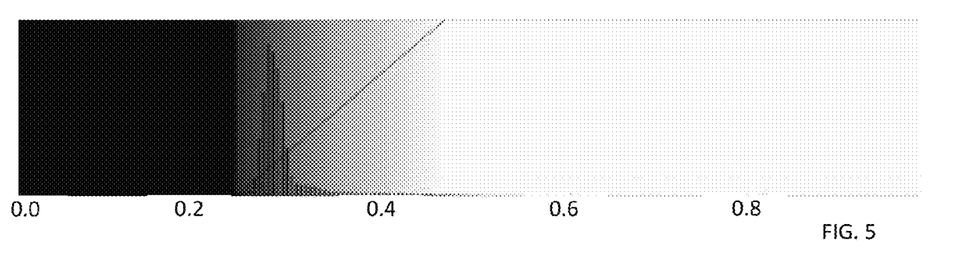
FIGS. 5 and 6 show the example transfer functions of FIGS. 3 and 4 overlaid with a histogram of intensities for voxels corresponding to a region of interest in a rendered image.

FIG. 3 shows a transfer function 29 for an initial rendering. The scalar values below lutMin are mapped to completely transparent, and the values above lutMax are mapped to totally opaque. In between lutMin and lutMax, different scalar values map to different colors. FIG. 5 shows a histogram 37 from an ROI of FIG. 7 with the histogram overlaid on the transfer function of FIG. 3. The histogram scalar values are aligned with the transfer function scalar values. Most of the values of the histogram 37 fall within a narrow portion of the window width.

Figure 4:
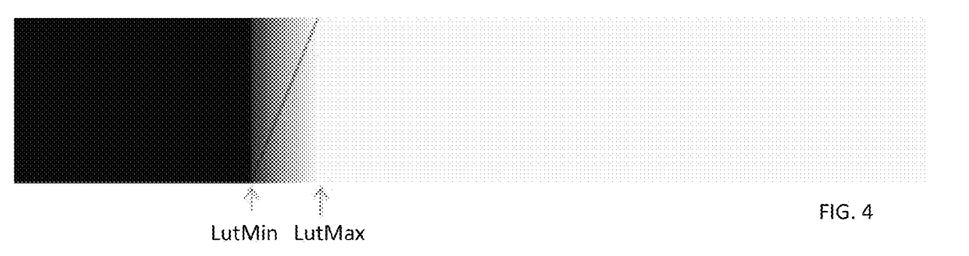
Figure 6:
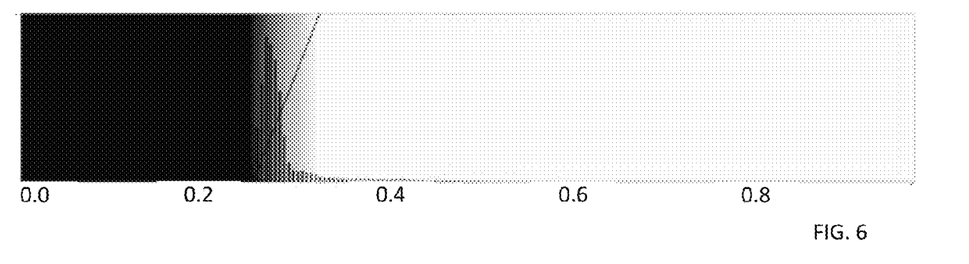

To increase contrast, the window width is reduced, and the window level is centered about the mean. Using the window width and level formulas above, a new window width and a new window level are determined. FIG. 4 shows the new transfer function 29. The width is decreased, and the center of the window is shifted to a lower scalar value. FIG. 6 shows the new transfer function 29 with the overlaid histogram. The window is positioned to capture most of the intensities for voxels corresponding to the ROI (i.e., capture the larger count bins of the histogram). To increase the contrast, the outliers of the intensities (e.g., more than a standard deviation) are mapped to opaque and transparent. Most of the significant (i.e., remaining) scalar values or intensities are distributed over a greater number of colors and/or opacities. Other mappings may be used, such as maintaining higher or lower intensities in the window.

Figure 8:
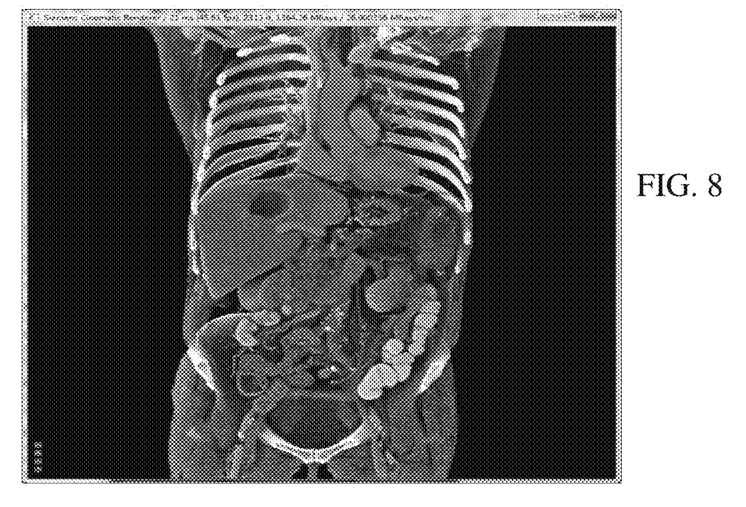

FIG. 7 shows an initial ray tracing rendering using the transfer function 29 of FIG. 3. The initial rendering uses a default window width and level for the imaging application. FIG. 8 shows a new ray tracing rendering using the transfer function 29 of FIG. 4. The contrast is drastically increased in FIG. 8 as compared to FIG. 7 for the soft tissue of the selected ROI (shown in FIG. 7). The smaller width centered on the intensities of the voxels for the ROI provides for greater contrast for the tissue of the ROI. The modified transfer function based on the local histogram for the selected ROI provides greater contrast.

In one embodiment, the transparency, such as transparency range, is changed. It is often desired to modify the transparency of certain tissues to display structures hidden behind them. The ROI is used to specify the tissue to be removed by opacity modification of the transfer function 29. The distribution of scalar values of corresponding to the ROI is used to modify the corresponding opacity values on the transfer function 29. The opacity modification may be used with or without window or other modifications of the transfer function 29.

Any function may be used to map the distribution to the transparency. For example, Imin and Imax define a range of scalar values where increased transparency is to be provided. The transparency range of one embodiment is determined to include a majority of the histogram 37. In one embodiment, transparency range is defined as:

$$Imin = (roiMin - W'l)/W'w; \text{ and}$$

$$Imax = (roiMax - W'l)/W'w$$

A default or user set amount of change in transparency is used. Alternatively, the amount of transparency increase within the range is based on the distribution, such as greater transparency for scalar values having a greater occurrence in the distribution. The increase is relative to the initial transfer function through a change in the window level and/or width. Other functions or mappings may be used, including a function based on distribution without change in width and/or level.

Figure 11:
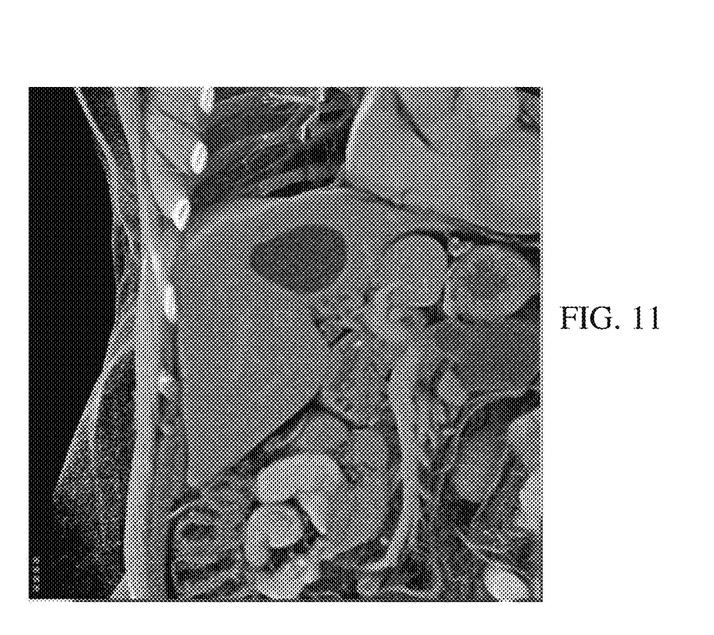
FIGS. 11 and 12 show example images based on change in opacity.
Figure 12:
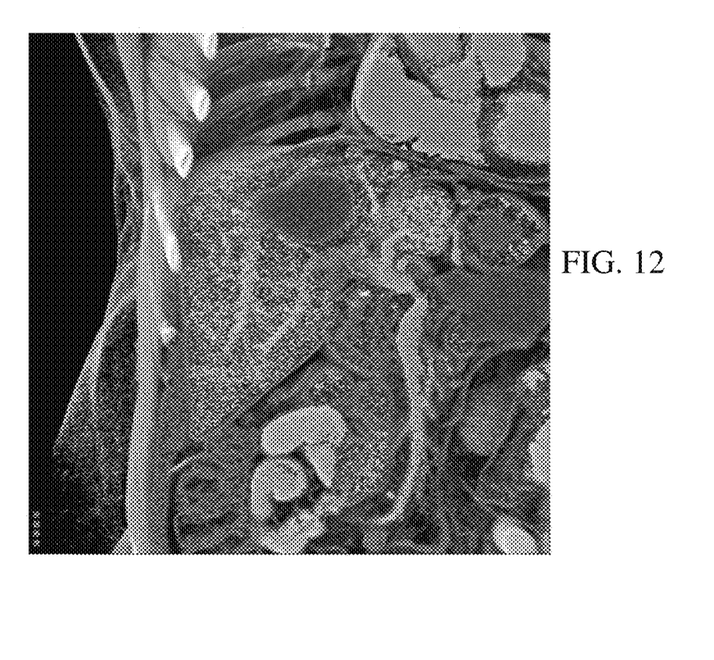

FIGS. 11 and 12 show example images of opacity modification. FIG. 11 represents a ray tracing rendering with an initial transfer function 29. The ROI is positioned on liver soft tissue that occludes vessel structures within the liver. In addition to calculating the window level and width to increase contrast, a transparency range is also calculated using the formulas above. FIG. 12 represents the same scan data re-rendered using ray tracing with the modified transfer function 29. By positioning the ROI over the liver tissue, the transfer function is modified to make this tissue more transparent. Anatomical structures, such as vessels and arteries, previously hidden behind this tissue become visible.

Multi-dimensional transfer functions may be used and modified based on the intensities of voxels corresponding to a ROI of the initially rendered two-dimensional image. Multi-dimensional transfer functions use various characteristics of the scan data to determine color or other characteristics of the transfer function 29. For example, intensities are mapped to color. The segmentation, shape, magnitude, gradient, and/or curvature of structure represented by the intensities also controls the color. Any multi-dimensional transfer function may be used. Multi-dimensional transfer functions help differentiate tissues with overlapping intensities. As the dimensionality of the transfer function increases, so does the complexity of using and defining the multi-dimensional transfer function.

One or more characteristics of the multi-dimensional transfer function are determined based on one or more (e.g., different) characteristics of the intensities of the voxels of the subset. For example, the scalar values, local gradients of the scalar values, and curvature represented by the scalar values of the voxels of the subset are mapped or related by a function to the transfer function. Different transfer functions are provided for different combinations of distribution of scalar values, gradients, and/or curvature. When an ROI is selected, not only the corresponding scalar values are analyzed but also other information, such as the local gradient and curvature.

Figure 13:
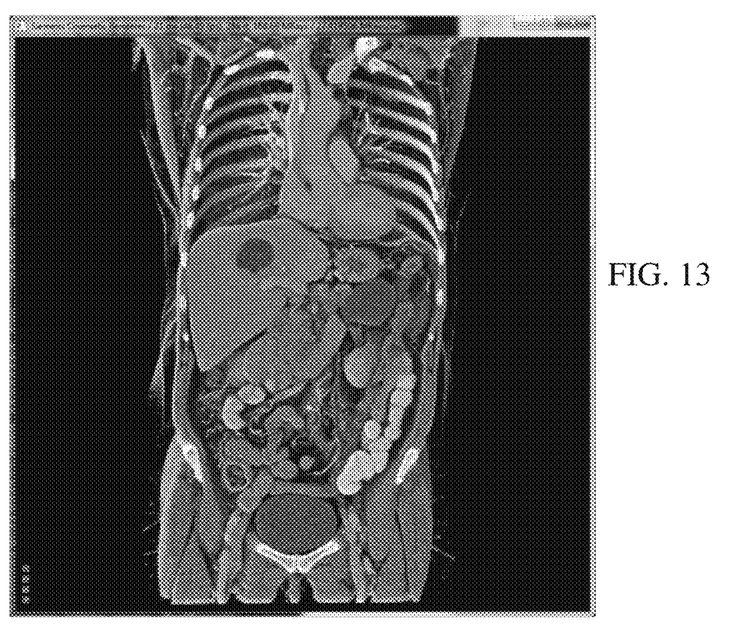
FIGS. 13 and 14 show example images based on change in color map of the transfer function.
Figure 14:
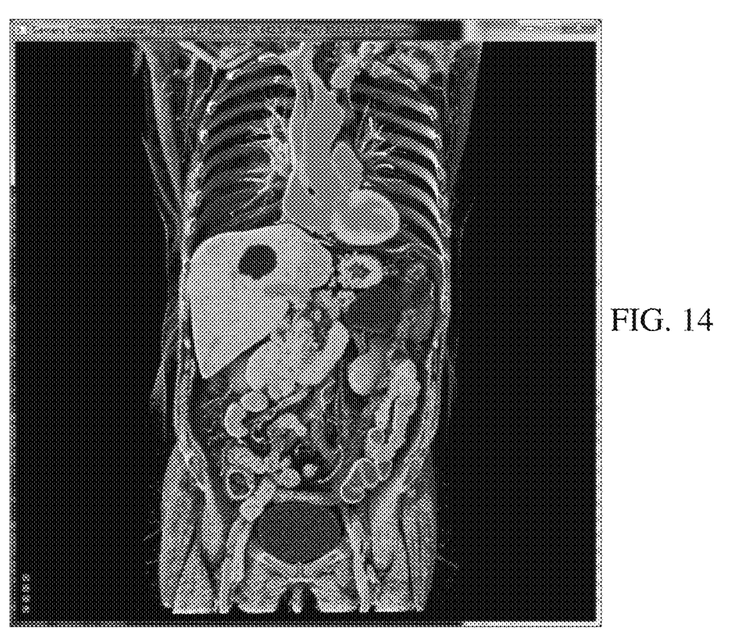

In one embodiment, the color pallet is changed. Using a wider range of colors may help distinguish between types of tissue. Rather than rendering to emulate the tissue as if being actually lit by a light source (e.g., red color pallet), the transfer function is changed in color pallet to render as if lit by different light sources or type of light. Any function may be used to map the distribution to the color pallet. For example, a ROI is selected. The resulting distribution is used to select a color pallet that will provide more contrast or color separation of the selected structure from other structures. RGB values are assigned to the corresponding transfer function intensity range. FIG. 13 shows an example ray tracing rendering using a red color pallet. To better highlight the liver, the ROI is positioned on the liver. The transfer function 29 is modified by selecting a green, red, blue color pallet. FIG. 14 shows an example ray tracing rendering using the modified color pallet.

In act 40, the graphics processing unit renders another two-dimensional image using the new or modified transfer function. The rendering uses the same or different (e.g., subsequently acquired) scan or voxel data. Since a new transfer function is being used, the rendered two-dimensional image has a different appearance. More contrast for the tissue or structure of interest may be provided. Less occlusion by selected tissue or structure may occur. Different coloring to better distinguish tissues may be used.

The rendering reduces the three-dimensional distribution of scalar values (i.e., voxels) to a two-dimensional image 33 (i.e., pixels). The same type of rendering as for the initial rendering is used, but a different type of rendering may be used. For example, ray tracing with Monte Carlo emulation of photon interaction with the intensities representing the volume is used for both renderings.

The two-dimensional image 33 is rendered to a display, but may be transmitted to memory or over a computer network. The two-dimensional image 33 is used for diagnosis and/or prognosis. The change in the transfer function may allow for more informed diagnosis and/or prognosis by providing additional or different information due to the change in the transfer function. The two-dimensional image 33 is shown by itself or is shown adjacent to one or more other two-dimensional images 33, such as renderings of the same scan data with different transfer functions.

The two-dimensional image 33 is rendered using the new or modified transfer function. Since the transfer function is based on the intensities of a subset of voxels corresponding to a ROI in a previously rendered two-dimensional image, the two-dimensional image 33 more likely provides information about the desired tissue or structure. The transfer function may be based, in part, on other information, such as a depth of a surface depicted in the previous two-dimensional image 33, curvature, and/or gradients.

The two-dimensional image 33 is rendered with a different window level, window width, transparency range, transparency level, color pallet, and/or another characteristic of the transfer function 29. For example, the transparency range is altered. The intensities of voxels in a particular range based on the ROI-based subset are rendered as more transparent. The result is less occlusion. FIGS. 8, 12, and 14 represent ray tracing renderings using different transfer functions and the same scan data than the ray tracings of FIGS. 7, 11, and 13.

The return line from act 40 to act 34 of FIG. 1 represents repetition. Another ROI may be received, resulting in identifying another subset of voxels. Another transfer function is determined based on the voxel intensities of the other subset. The image is rendered again with the different transfer function. During use, a radiologist or other viewer may explore the volume of the patient by different renderings of the scan data. Different tissues or structures may be of interest. The mapping between the scalar values and the color of the rendered image may be interactively modified to create multiple two-dimensional images 33 using multiple transfer functions 29. By efficiently computing the optimal windowing parameters for a particular ROI, the volumetric data is explored. For example, by moving the mouse to different regions of the initial or other image, different ROIs are selected and the system automatically re-computes the optimal windowing parameters. Multiple views are generated by placing ROIs on different tissue types. Other repetitions may be used, such as repeating the initial rendering, repeating the scanning to acquire new scan data, or repeating to alter the type of characteristics of the transfer function and/or distribution to be used.

Figure 9:
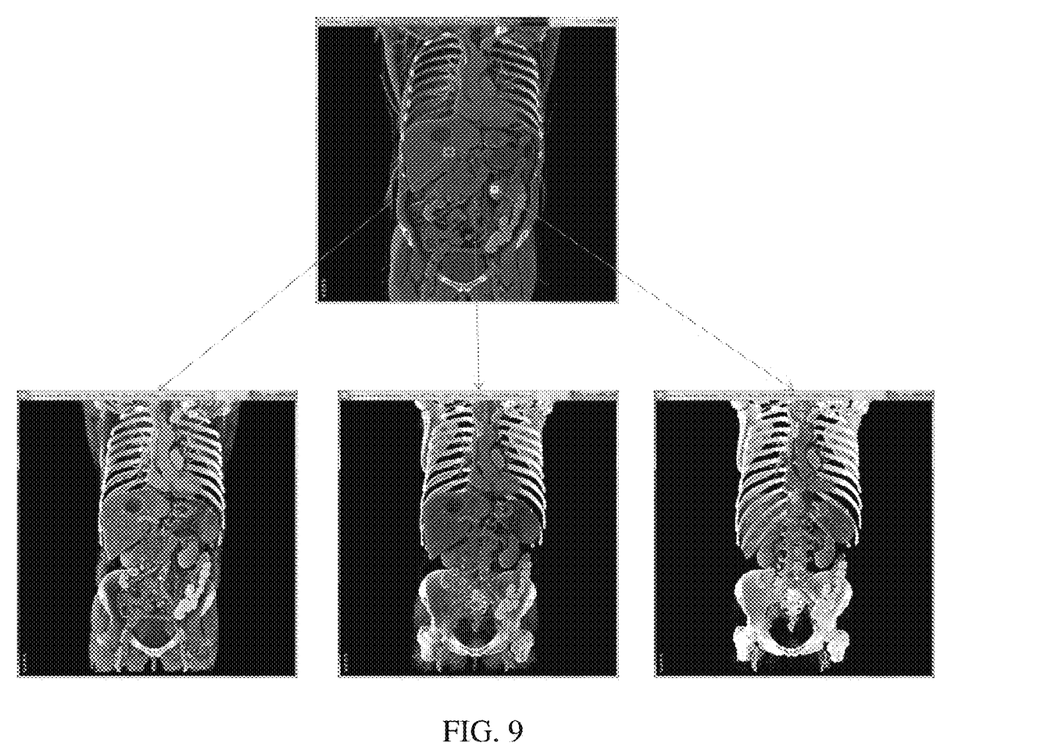
FIGS. 9 and 10 show example rendered images as part of exploration by repositioning a region of interest and rendering with different transfer functions based on the regions of interest.
Figure 10:
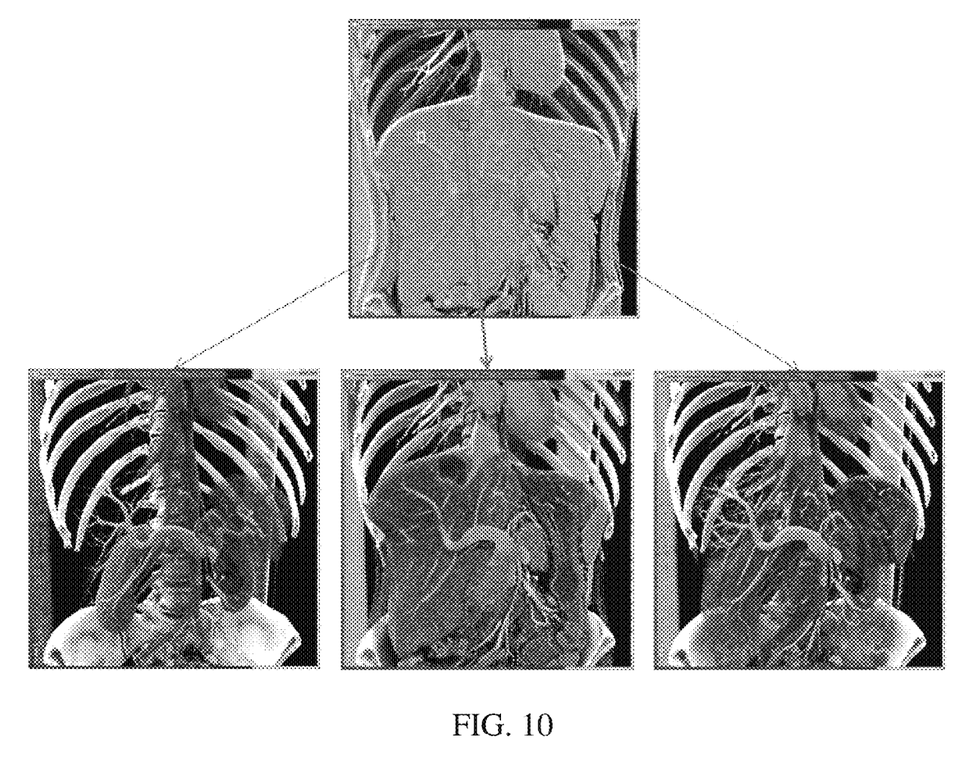

FIGS. 9 and 10 show example ray tracing renderings. The initial image is shown with three ROIs. Due to the differences in the scan data linked to the ROIs, three different transfer functions are determined. The bottom row of three ray tracing renderings shows two-dimensional images rendered from the same scan data with the different transfer functions. For each of the different transfer functions, the window level and width are modified. By selecting different ROIs, the viewer or processor may navigate through the scan data or explore the volumetric data to view different tissue with greater contrast. Making one structure have greater contrast may result in other structures having less contrast, so repositioning the ROI alters the range of scalar values to have greater contrast.

FIG. 15 shows one embodiment of a system 10 for rendering in medical imaging. The system 10 renders a volume of a patient for medical visualization. Using voxel data selected based on a ROI in a rendered image, the transfer function for rendering is modified or set. The resulting transfer function is used to render another image, which may better present information of interest. The system 10 is configured to implement the method of FIG. 1 or the method of FIG. 2. Alternatively, other methods are implemented.

The system 10 includes a medical imaging system 12, a user interface or input 14, a renderer 16, a memory 18, and a display 20. Additional, different, or fewer components may be provided. For example, a network or network connection is provided, such as for networking with a medical imaging network or data archival system. As another example, the user interface 14 is not provided, and the selection of ROI is performed by a processor, such as the renderer 16 or a processor of the medical imaging system 12.

The user interface 14, renderer 16, memory 18, and display 20 are part of the medical imaging system 12. Alternatively, the user interface 14, renderer 16, memory 18, and/or display 20 are part of an archival and/or image processing system, such as associated with a medical records database workstation or server. In other embodiments, the user interface 14, renderer 16, memory 18, and/or display 20 are a separate computer, such as desktop or laptop, a workstation, a server, or combinations thereof. The user interface 14, renderer 16, memory 18, and display 20 may be parts of different systems, such as the memory 18 being in a picture archiving and communications system (PACS), the renderer 16 being part of a workstation, and/or the display 20 being an imaging system or radiological display.

Any medical imaging system 12 may be used. For example, the medical imaging system 12 is a CT, MR, ultrasound, x-ray, fluoroscopy, angiography, or emission tomography (i.e., functional imaging such as PET or SPECT) system. The medical imaging system 12 is any now known or later developed medical imaging system for scanning an interior of the patient.

The medical imaging system 12 is configured by hardware, firmware, and/or software to scan the internal region of a patient and generate voxel data representing a scanned volume of the internal region. The voxel data represents a three-dimensional sampling of the volume. The surface or skin of the patient may or may not also be scanned. Any portion or extent of the patient may be scanned, such as a scan of an organ, torso, extremity, or full body.

The medical imaging system 12 is configured to scan the patient to acquire at least one set of data. The set or frame of data represents the internal region of the patient at a specific time or period. A static volume is acquired. Alternatively, the scanning is repeated or performed in an ongoing manner to acquire a sequence of sets of voxel data. Each set represents the volume at a given time or period, so the sequence represents the volume over time (3D+t or 4D data). Any frame or volume rate may be provided. For real-time rates, at least 10 volumes or sets of voxel data are acquired each second. Greater or lesser volume rates may be provided.

The scan data may be output as a 3D reconstruction or data representing a volume. Alternatively, the acquired scan data is reconstructed to represent the volume. For example, Fourier processing is applied to k-space data in MR to reconstruct the volume. As another example, computed tomography is used to reconstruct the volume (e.g., SPECT or CT). In yet another example, data representing three dimensions in a scan format is interpolated to a regular or other grid, such as a Cartesian coordinate grid. Each datum is associated with a different volume location (voxel) in the patient volume and assigned a scalar intensity.

The data from the scan is formatted as voxels in an isotropic grid. For example, voxels in a 512×512×512 Cartesian grid are used. Anisotropic grids may be used. Other formats may be used, such as the data representing locations in a polar coordinate format. For each voxel or location, a scan response is provided by a scalar value (e.g., 16-bit dynamic range), but other representations may be used, such as RGBα values.

Given the number of different types of medical imaging systems 12, different workflows, different clinical applications, and use for diagnosis or treatment, there is a large variety in the voxel data and characteristics of the voxel data in medical imaging. Any one or more sets of voxel data representing intensity of return, density, attenuation, elasticity, motion, uptake, temperature, molecular spin response, other characteristics, or combinations thereof may be acquired by the medical imaging system 12.

The user interface 14 is an input device with or without an output. Any input may be used, such as keyboard, button, slider, knob, track pad, mouse, track pad, or other sensor. The output may be on the display 20, an LED, light, or other output.

The user interface 14 is configured to receive input from the user. The input may configure the rendering. The user inputs a value or values for any number of rendering parameters, such as view direction, type of lighting, visual effect, and/or transfer function. For example, the user may interactively change one or more values of a setting. In one embodiment, the user rotates or alters the view direction for rendering. In other embodiments, the user selects the imaging application (e.g., cardiac imaging), resulting in loading of default settings. In alternative embodiments, a processor or the renderer 16 uses default or determines values for one, more, or all the settings.

In one embodiment, the user interface 14 is configured to receive a selection of a ROI. Using a pointer, the user positions and sizes an area designator. For example, a box or oval is positioned and sized using click and drag. As another example, the user traces an outline. Alternatively, the ROI is positioned and sized by the renderer 16 or another processor.

The renderer 16 is a general processor, central processing unit, control processor, graphics processor, graphics processing unit, digital signal processor, three-dimensional rendering processor, image processor, application specific integrated circuit (ASIC), field programmable gate array (FPGA), digital circuit, analog circuit, combinations thereof, or other now known or later developed device for rendering an image from data. The renderer 16 is a single device or multiple devices operating in serial, parallel, or separately. The renderer 16 may be a graphics card performing parallel processing for rendering, or may be a processor for handling some tasks in a larger system, such as in the medical imaging system 12. The renderer 16 is configured by hardware, firmware, and/or software.

In one embodiment, the renderer 16 is a graphics processing unit (GPU) or a graphics card with rendering code. A set of graphics cards may be used. A GPU is a massively parallel computation device. CUDA or OpenCL languages are used to program the GPU. In other embodiments, the x86-based Xeon Phi or custom FPGA/ASIC implementations are used. Multiple GPUs in a render node, GPU clusters, CPU/GPU hybrid systems, or other computational architectures may be used. Sample-based, tile-based, or frame-based distribution of the rendering may be used.

The renderer 16 is configured to render a two-dimensional image from the three-dimensional distribution of voxel data. Any rendering may be used, such as ray or path tracing, physical-based, maximum intensity projection, or ray casting. The physical rendering uses a physics model, such as for photon or another path tracing, to render. Rays are traced from each of a plurality of pixels for the image, and the interaction of the light photon with the volume is modeled. For example, probabilities are used to model interaction.

The rendering by the renderer 16 is based, in part, on a transfer function. The transfer function defines the mapping of color from the scalar values of the voxel data, including a window level, window width, transparency level, transparency range, and/or color pallet. One or more parameters of the transfer function are set based on part of the voxel data of the volume. The part is selected based on a selection of a region in a rendered image. For example, a portion of a rendered image is selected. Using a depth map, the scalar values for voxel data along a surface represented in the portion are extracted from the voxel cache. The scalar values are histogrammed. Other distributions of the scalar values may be used. The histogram or other distribution information maps to settings for the transfer function. The transfer function is selected (e.g., previous transfer function is modified or a new transfer function created) based on the distribution information. For example, the window level and/or window width are set based, in part, on the distribution of scalar values corresponding to the ROI.

The renderer 16 generates a two-dimensional image or sequence of images representing the internal region of the patient. For example, one of the images of FIGS. 7-14 is output. A given image represents the internal region at a specific time or period. The sequence of images may be for a static volume with different transfer functions or for real-time imaging over time with different transfer functions. The generated images are display color values (e.g., RGB) for pixels based on the scalar values for the voxels. The images are output by transfer or loading into a display buffer.

The display 20 is configured to display the image output by the renderer 16. The display 20 is a monitor, LCD, projector, plasma display, CRT, printer, or other now known or later developed devise for outputting visual information. The display 20 is configured by receiving images, graphics, or other information from the renderer 16, memory 18, or medical imaging system 12. The display 20 receives the image rendered from the volume scan. The image is output to the user.

The memory 18 is a graphics processing memory, video random access memory, random access memory, system memory, cache memory, hard drive, optical media, magnetic media, flash drive, buffer, database, combinations thereof, or other now known or later developed memory device for storing data. The memory 18 is part of the medical imaging system 12, part of a computer associated with the renderer 16, part of a database, part of another system, or a standalone device.

The medical scan data, reconstruction, voxel data, frames, rendering, settings, transfer function, subset selection, ROI information, distribution, and/or images are stored. Any data used for imaging or data in beginning, intermediate, or final stages of processing are stored for access by the renderer 16.

The memory 18 or other memory is a non-transitory computer readable storage medium storing data representing instructions executable by the programmed renderer 16 for rendering in medical imaging. The instructions for implementing the processes, methods, and/or techniques discussed herein are provided on computer-readable storage media or memories, such as a cache, buffer, RAM, removable media, hard drive, or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for rendering an image from a medical scanner, the method comprising:
   scanning a volume of a patient by the medical scanner, the scanning providing intensities representing voxels of the volume;
   rendering, by a graphics processing unit, a first two-dimensional image from the intensities representing the voxels, the rendering using a first transfer function;
   receiving a region of interest determined based on the first two-dimensional image;
   identifying a subset of the voxels from a voxel cache that includes a depth map of the voxels for a surface of an object in the volume of the region of interest;
   determining a second transfer function from a distribution of the intensities of the voxels of the subset; and
   rendering, by the graphics processing unit, a second two-dimensional image using the second transfer function.

2. The method of claim 1 wherein scanning comprises scanning with computed tomography, positron emission tomography, single photon emission computed tomography, x-rays, magnetic resonance, or ultrasound.

3. The method of claim 1 wherein scanning the volume comprises obtaining the intensities representing a three-dimensional distribution of the voxels in the volume, and wherein rendering the first two-dimensional image comprises rendering to the first two-dimensional image as pixels in a two-dimensional distribution from the three-dimensional distribution.

4. The method of claim 1 wherein rendering the first and second two-dimensional images comprises rendering with the first and second transfer functions comprising different window levels and/or different window widths.

5. The method of claim 1 wherein rendering the first and second two-dimensional images comprises rendering with the first and second transfer functions comprising different opacity ranges.

6. The method of claim 1 wherein rendering the first and second two-dimensional images comprises rendering with Monte Carlo emulation of photon interaction with the intensities representing the volume.

7. The method of claim 1 wherein receiving the region of interest comprises receiving, via a user input device, a user selection of material based on occlusion or contrast.

8. The method of claim 1 wherein receiving comprises receiving the region of interest as an automated detection of material represented in the first two-dimensional image, the automated detection being based on occlusion or contrast.

9. The method of claim 1 wherein determining comprises determining from a Gaussian curve fit to the intensities of the voxels of the subset as the distribution of the intensities.

10. The method of claim 9 wherein determining comprises determining a window width of the second transfer function from a mean and standard deviation of the Gaussian curve and a window width of the first transfer function, and determining a window level of the second transfer function from the window width of the second transfer function, the mean, and the window width of the first transfer function.

11. The method of claim 1 wherein determining comprises determining the second transfer function as a multi-dimensional transfer function with different dimensions being based on different characteristics of the intensities of the voxels of the subset.

12. The method of claim 1 further comprising repeating the receiving for another region of interest, identifying for another subset, determining for a third transfer function, and rendering for the third transfer function.

13. The method of claim 1 wherein rendering the second two-dimensional image comprises rendering the intensities representing the voxels.

14. The method of claim 1 wherein rendering the second two-dimensional image comprises rendering onto a display device.

15. The method of claim 1 wherein determining the second transfer function comprises determining a transparency range, and wherein rendering comprises rendering with the intensities of the voxels for the subset as more transparent with the second transfer function than the first transfer function due to the transparency range.

16. A system for rendering in medical imaging, the system comprising:
a medical imaging system configured to scan an internal region of a patient and generate voxel data representing a volume comprising the internal region;
a renderer configured to render a first image from the voxel data, the renderer configured to render with a transfer function setting based on data related to a subset of voxels from a voxel cache that includes a depth map of voxels for a surface of an object in a part of a region in a second image; and
a display configured to display the rendered first image output by the renderer, the rendered first image representing the internal region.

17. The system of claim 16 wherein the transfer function setting is a window level and/or window width with the part being voxel data for a surface of the internal region designated by the region and depth.

18. The system of claim 16 wherein the data relating to the part comprises a histogram distribution of scalar values of the voxel data.

19. A method for rendering in medical imaging, the method comprising:
scanning a volume of a patient by a medical scanner, the scanning providing intensities representing voxels of the volume;
rendering, by a graphics processing unit, a first two-dimensional image from the intensities representing the voxels, the rendering using a first transfer function; and
rendering, by the graphics processing unit, a second two-dimensional image using a second transfer function, the second transfer function set as a function of the intensities of a subset of the voxels identified from a voxel cache that includes a depth map of voxels for a surface of an object in a region of interest on the first two-dimensional image and a depth of a surface depicted in the first two-dimensional image.

* * * * *